(12) United States Patent
Klocke

(10) Patent No.: US 11,452,281 B2
(45) Date of Patent: Sep. 27, 2022

(54) PIGLET EAR-TAGGING STATION

(71) Applicant: Dave Klocke, Templeton, IA (US)

(72) Inventor: Dave Klocke, Templeton, IA (US)

( * ) Notice: Subject to any disclaimer, the term of this patent is extended or adjusted under 35 U.S.C. 154(b) by 913 days.

(21) Appl. No.: 16/260,641

(22) Filed: Jan. 29, 2019

(65) Prior Publication Data

US 2019/0239477 A1 Aug. 8, 2019

Related U.S. Application Data

(60) Provisional application No. 62/623,797, filed on Feb. 8, 2018.

(51) Int. Cl.
  *A01K 11/00* (2006.01)
  *A61M 37/00* (2006.01)

(52) U.S. Cl.
  CPC ....... *A01K 11/002* (2013.01); *A61M 37/0069* (2013.01)

(58) Field of Classification Search
  CPC ................ B30B 1/04; Y10T 74/20189; Y10T 74/20528; A01K 11/002; A61M 37/0069
  See application file for complete search history.

(56) References Cited

U.S. PATENT DOCUMENTS

| | | | | |
|---|---|---|---|---|
| 1,675,444 A * | 7/1928 | Blando | ...................... | B30B 1/04 100/286 |
| 1,721,917 A * | 7/1929 | Mcdonough | .............. | B30B 1/04 74/512 |
| 1,818,837 A * | 8/1931 | Barker | ...................... | B30B 1/04 269/238 |
| 2,283,553 A * | 5/1942 | Heidenfelder | .......... | D06F 71/02 38/25 |
| 2,345,731 A * | 4/1944 | Coyle | ................... | A47J 19/023 100/98 R |
| 2,533,870 A * | 12/1950 | Bayer | .................. | A44C 17/043 29/513 |
| 3,871,055 A * | 3/1975 | Dail | ........................ | B23P 19/04 29/226 |
| 4,561,177 A * | 12/1985 | Rancer | ................... | D05C 13/00 29/721 |
| 6,053,926 A * | 4/2000 | Luehrs | ................. | A01K 11/002 606/117 |
| 6,443,054 B1 * | 9/2002 | McCamey | ........... | A21C 11/006 425/383 |

FOREIGN PATENT DOCUMENTS

DE 19707752 A1 9/1997

OTHER PUBLICATIONS

F. (Nov. 9, 2011). [hot item] double-head foot-press button attaching machine (JZQ-3). Retrieved Mar. 24, 2022, from https://www.made-in-china.com/showroom/e0010009/product-detailRqGnlkLxqAVd/China-Double-Head-Foot-Press-Button-Attaching-Machine-JZQ-3-.html (Year: 2011).*
Internet Archive. Wayback Machine, https://web.archive.org/web/2011*/https://www.made-in-china.com/showroom/e0010009/product-detailRqGnlkLxqAVd/China-Double-Head-Foot-Press-Button-Attaching-Machine-JZQ-3-.html. (Year: 2022).*

* cited by examiner

*Primary Examiner* — Thomas McEvoy
(74) *Attorney, Agent, or Firm* — McKee, Voorhees & Sease, PLC

(57) ABSTRACT

An ear tagging station includes a cart or table having at least one tagging pliers mounted thereon. The pliers have jaws which are normally open to receive male and female tag parts. An actuating arm engages one of the plier handles. A foot pedal on the cart is depressed to lift the arm and thereby close the plier jaws so as to secure the ear tag to a piglet's ear.

9 Claims, 9 Drawing Sheets

PIGLET EAR-TAGGING STATION

CROSS-REFERENCE TO RELATED APPLICATIONS

This application claims priority to Provisional Application U.S. Ser. No. 62/623,797, filed on Jan. 30, 2018, which is herein incorporated by reference in its entirety.

FIELD OF THE INVENTION

The invention is directed toward a cart or table having a pair of pliers for holding male and female ear tag components, with a foot pedal for actuating the pliers so as to secure the ear tag components to the ear of a piglet or other small animal.

BACKGROUND OF THE INVENTIONS

Ear tags for piglets are well-known, and typically are manually applied with a hand operated tagging tool. For example, an example of a commercially available tagging tool is made by Destron Fearing, which is like a pair of pliers spring biased to the opened position, with the jaws each adapted to hold the male and female tag pieces. An operator can hold the piglet between his/her legs and hold the piglet's head with one hand while the other hand grips the tool and then squeezes the handles to insert the tag into the piglet's ear. This process is slow, and requires the operator to bend over, which puts strain on the back. A second person is sometimes utilized to provide another set of hands to load the male and female tag pieces into the tool jaws.

Therefore, there is a need in the industry for a device which makes the tagging process faster, easier, and safer.

Accordingly, a primary objective of the present invention is the provision of an ear tagging station for use in placing an ear tag in the ear of a piglet or other small or young animal.

Another objective of the present invention is a provision of an ear tagging station having a foot actuated pair of pliers to secure a conventional ear tag on a piglet.

A further objective of the present invention is the provision of ear tag pliers which can be actuated by a foot pedal while the operator holds a piglet or small animal.

Yet another objective of the present invention the provision of an ear tagging station having dual, alternating tagging pliers.

Still another objective of the present invention is a provision of a pig ear tagging station to be used by a two-person team so as to tag piglets in less time.

Another objective of the present invention the provision of a method of tagging a piglet ear wherein the operator can hold a piglet in both hands to position the ear for tagging with foot-actuated tagging pliers.

These and other objectives will become apparent from the following description of the invention

SUMMARY OF THE INVENTION

The ear tagging station of the present invention is intended for use with piglets and other small animals to place a conventional ear tag quickly and easily in the ear. The station includes a cart or table having at least one pair of tagging pliers mounted thereon. The male and female ear tag components are positioned on the open jaws of the pliers. The cart or table also includes a foot pedal which can be depressed to lift an arm so as to actuate the pliers, and thereby close the jaws to attach the ear tag components to the piglet's ear. The foot pedal is biased to a neutral, raised position, with the arm lowered and the pliers open. The operator can hold the piglet in his/her hands, with the ear between the plier jaws, and then step downwardly on the foot pedal so as to close the pliers jaws and apply the ear tag to the ear. When the operator steps off the pedal, the plier jaws automatically open due to the spring bias of the pliers. Then a new set of male and female tag components can be placed on the jaws for the next piglet.

DETAILED DESCRIPTION OF THE INVENTION

Figure 1:
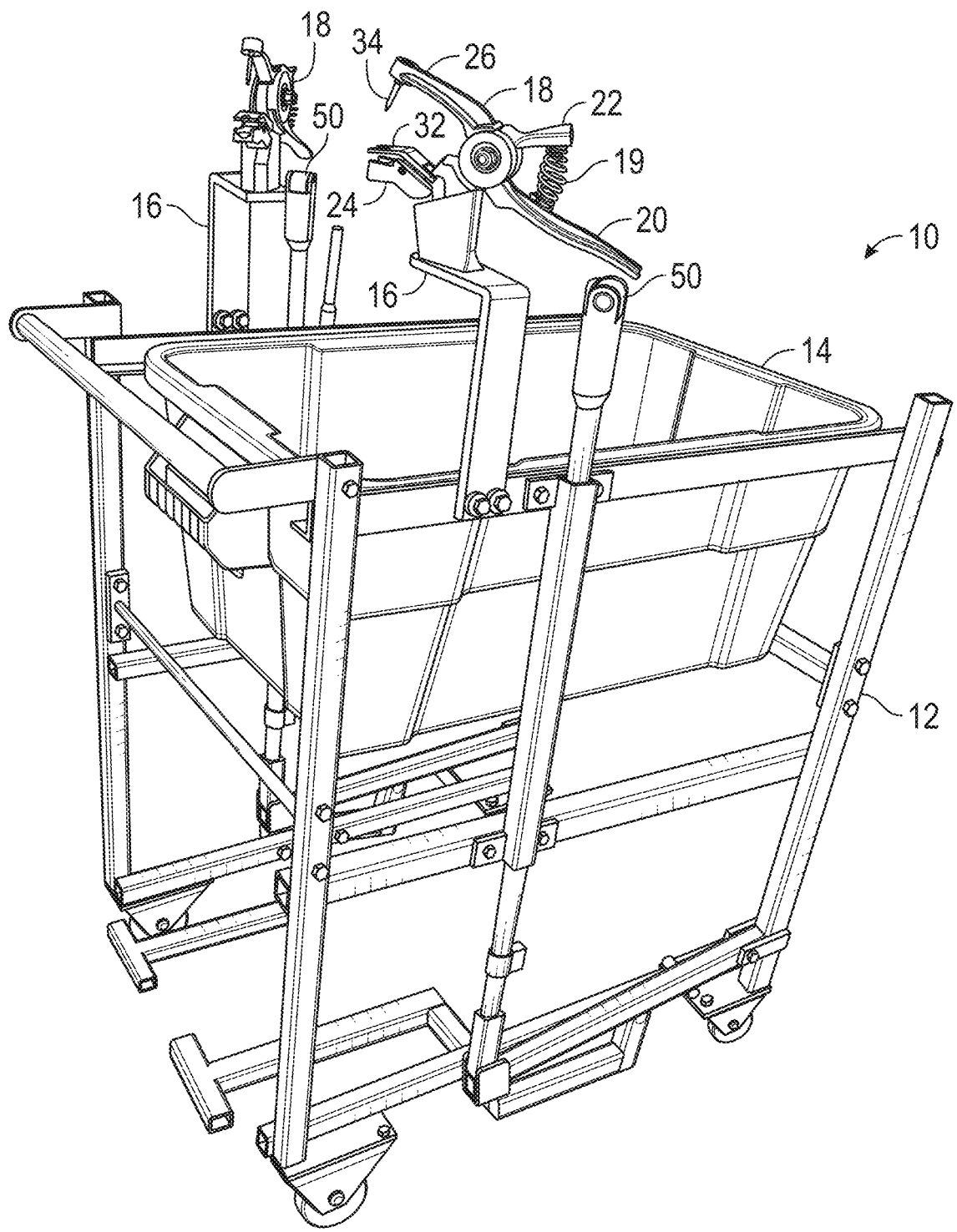
FIG. 1 is perspective view of a piglet ear-tagging station according to the present invention.
Figure 2:
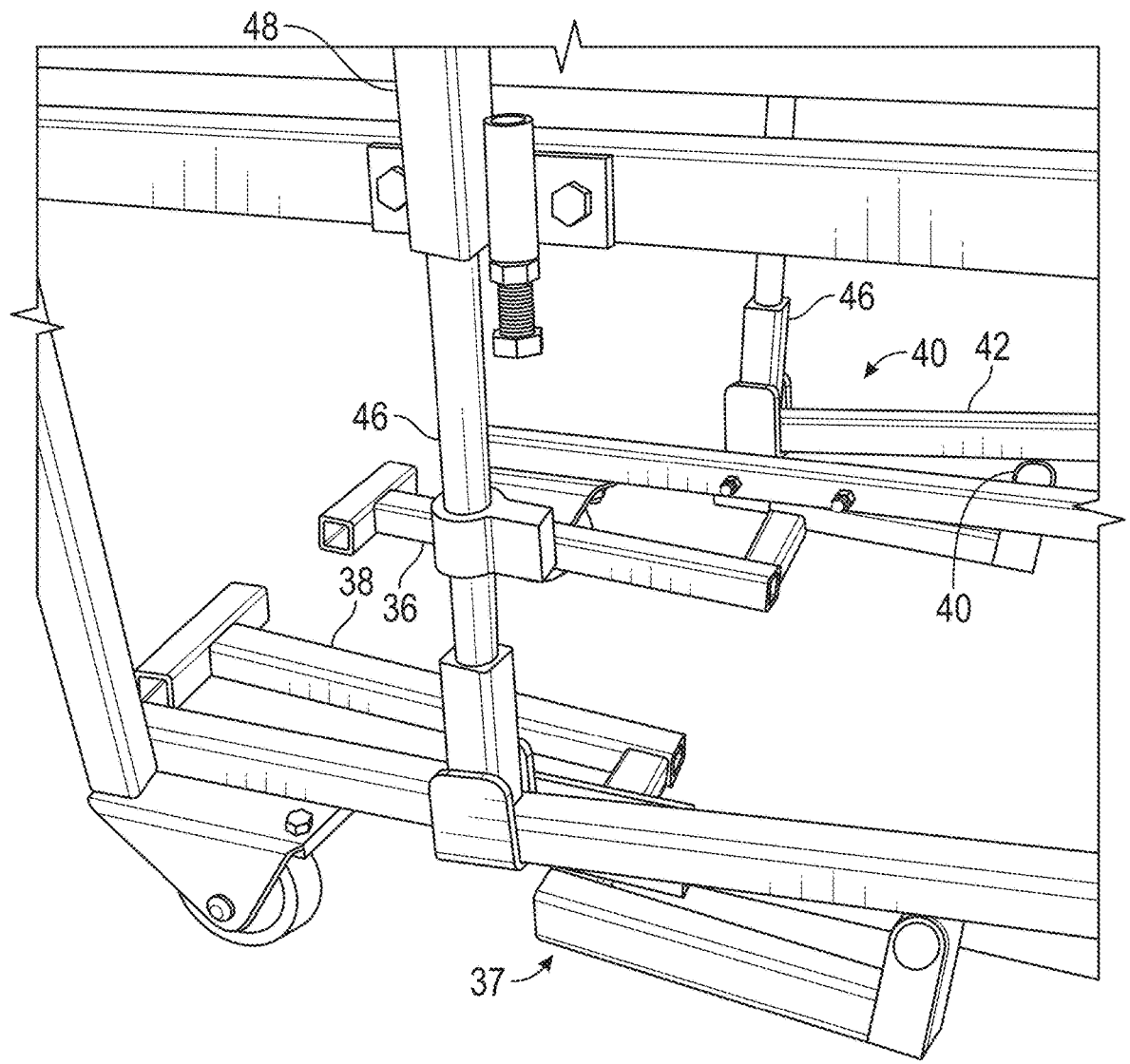
FIG. 2 is a view showing the base of the cart, with the foot pedals in the neutral, at-rest position.
Figure 3:
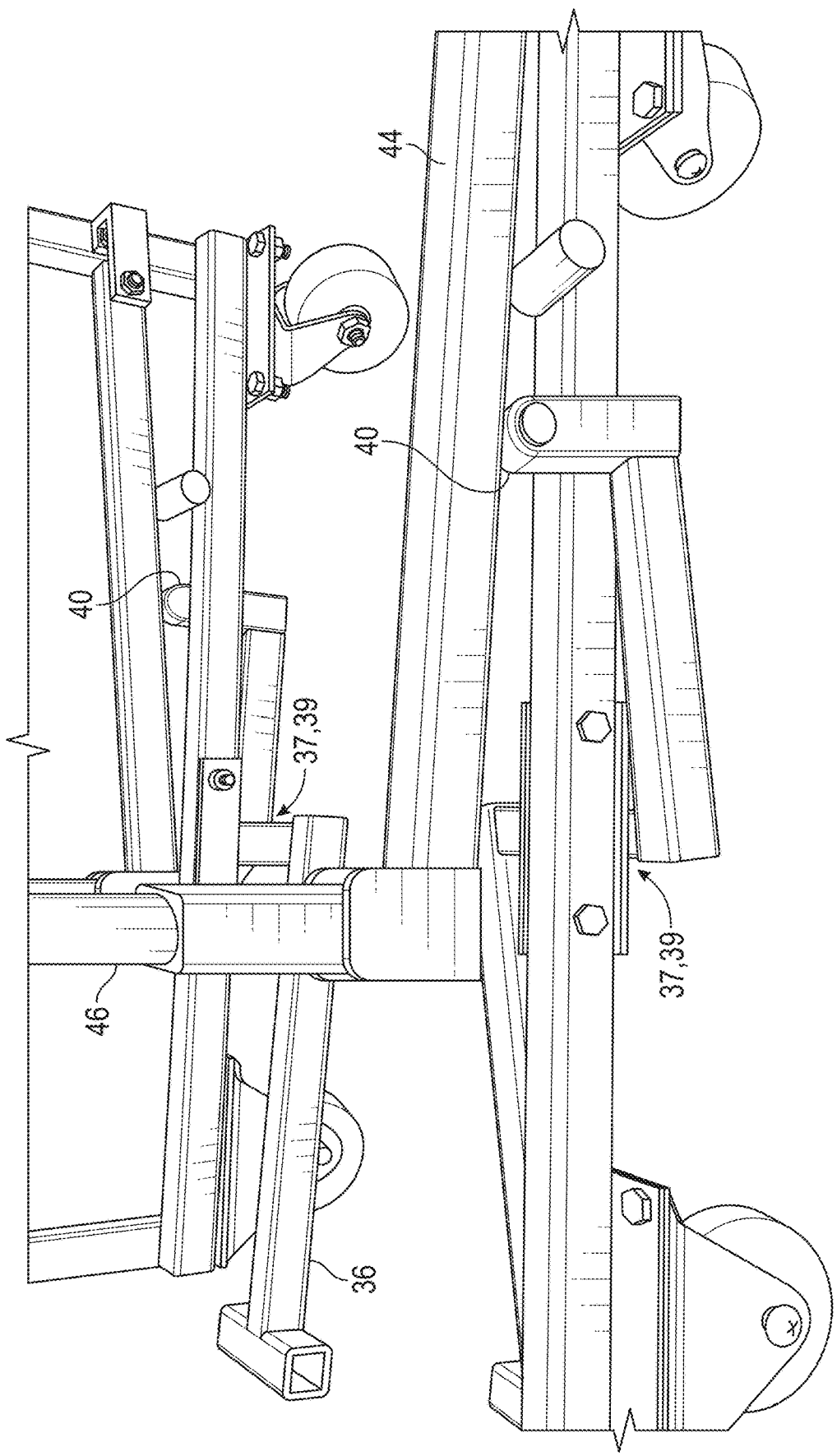
FIG. 3 shows one of the foot pedals in a depressed position to raise the lift arm and actuate the tagging pliers.
Figure 4:
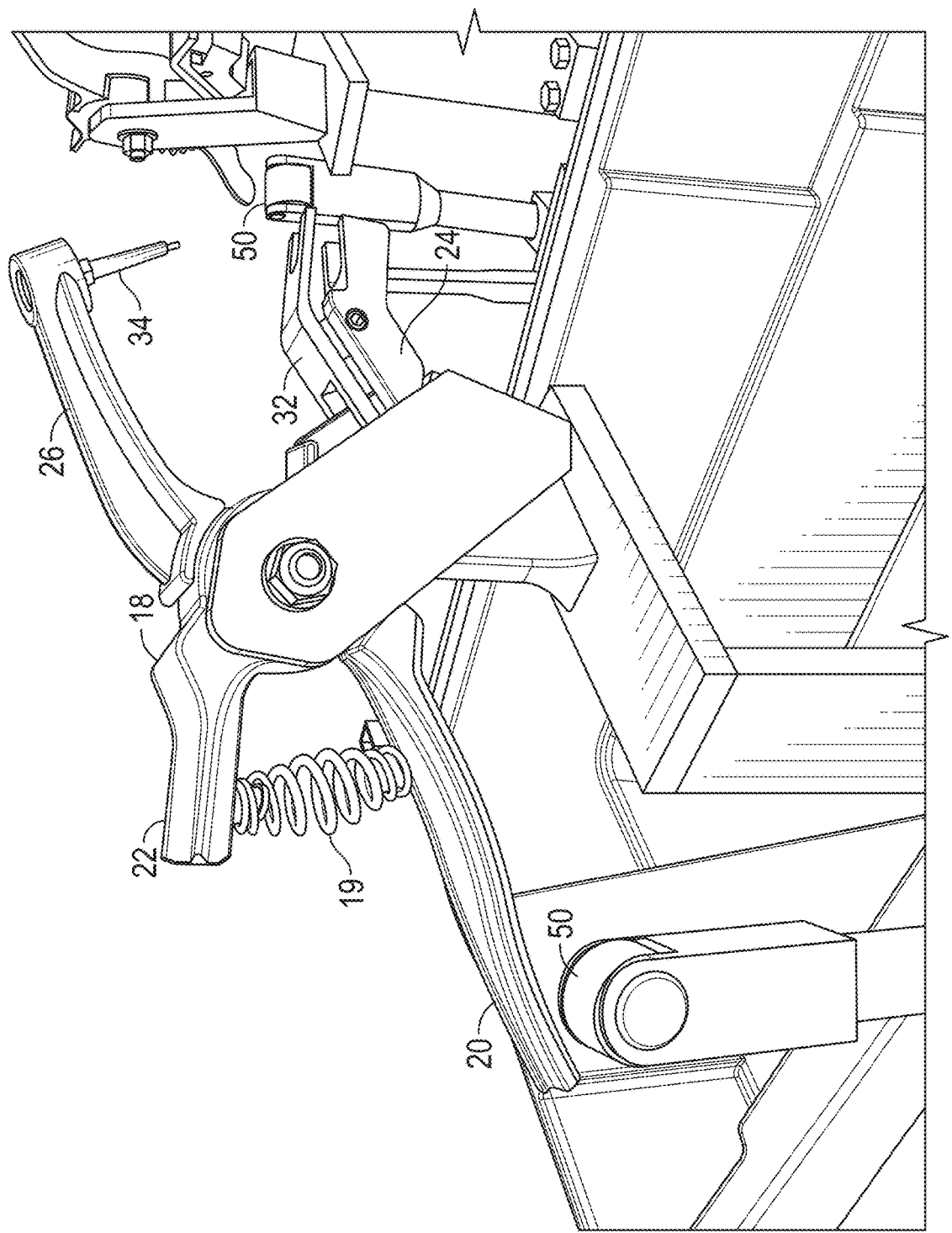
FIG. 4 shows the mounting bracket for the tagging pliers and the actuation roller.
Figure 5:
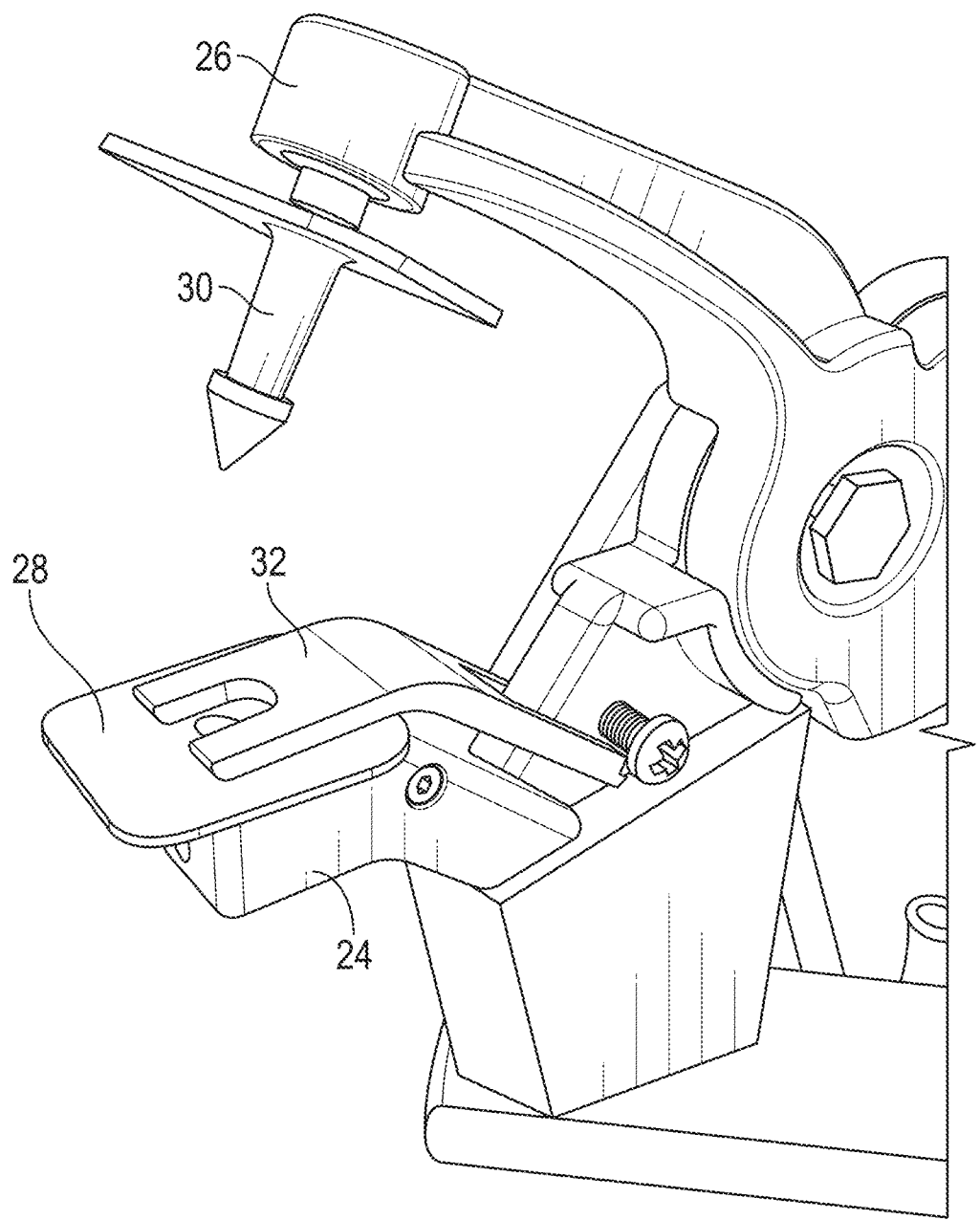
FIG. 5 shows the pliers from the opposite side of photograph 10, and with male and female ear tags components loaded into the pliers jaws.
Figure 6:
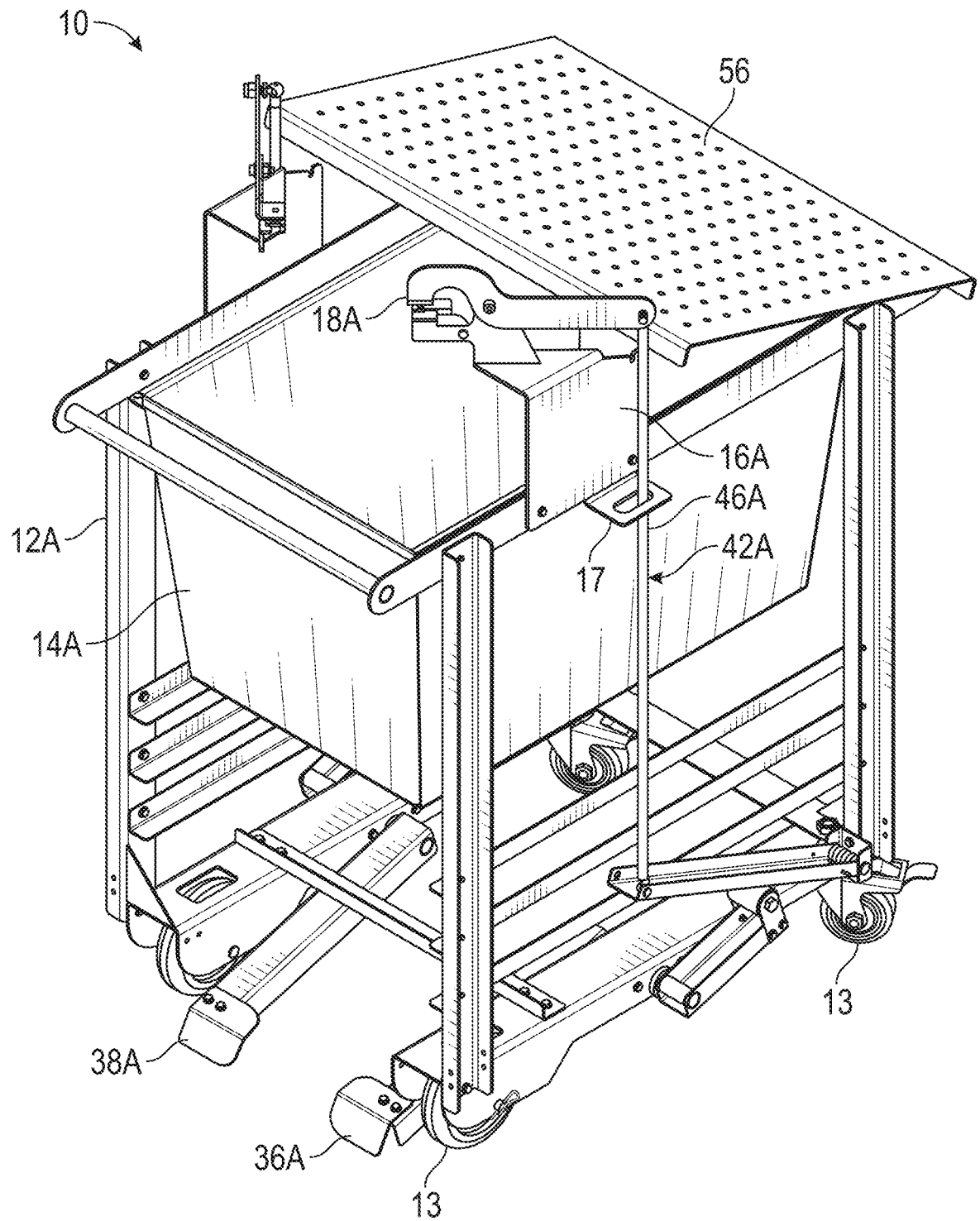
FIG. 6 is a perspective view of an alternative embodiment of the ear tagging station, according to the present invention.

The piglet ear-tagging station of the present invention is generally designated in the drawings by the reference numeral 10. The station 10 includes a cart or table 12 with a bin 14 having one or more compartments for easy access at the top of the cart. Each side of the cart 12 includes a bracket 16 extending upwardly. The bracket 16 may take various configurations, without departing from the scope of the invention. Preferably, the cart or table 12 is on lockable wheels 13 for rolling movement of the cart or table.

An ear-tagging tool 18 is mounted on each bracket 16. The tool 18 is generally in the form of a pair of pliers, with a lower handle 20 and an upper handle 22, which may be truncated or shortened. The tool 18 also includes a lower jaw 24 and an upper jaw 26 on the opposite ends of the handles 20, 22. The jaws 24, 26 are adapted to hold the female and male components 28, 30, respectively, of a conventional ear tag. For example, the lower jaw 24 includes a finger 32 to retain the female tag member 28, while the upper jaw 26 includes a pin 34 on which the male tag member 30 is frictionally retained. The jaws 24, 26 of the pliers 18 are biased by a spring 19 to an open position. Preferably, the station 10 has left and right tools 18 for alternating use.

The cart 12 includes left and right foot pedals 36, 38 for actuating the tools 18. The linkage between the foot pedals 36, 38 and the tools 18 can take various forms. For example, in a preferred embodiment, each foot pedal 36, 38 is pivotally mounted at the bottom of the cart 12 via an axle 37 journaled in a collar or bushing 39 and includes a roller 40 which engages the lower end of a lift arm assembly 42. The lift arm assembly 42 includes a lower arm 44 extending rearwardly near the bottom of the cart 12, and a vertical arm 48 connected to the forward end of the arm 44 and slidably extending through a guide tube 48 fixed to the sides of the cart 12. The upper end of the vertical arm 46 includes a roller 50 adapted to engage the lower handle 20 of the tool 18. Another alternative for connecting the foot pedals to the tools is a vertical rod with a tie rod or ball joints at each end.

In use, a first person can stand to the rear of the cart 12, or on either side, to load the female and male ear tag components 28, 30 onto the jaws 24, 26 of each tool 18. A second operator stands upright at the front of the cart 12 and holds a piglet so as to position the piglet's ear between the jaws 24, 26. The second person then actuates one of the tools 18 by stepping down on the respective foot pedal 36 or 38, which pivots about the axle 37, such that the roller 40 pushes the arms 44, 46 upwardly, whereby the roller 50 pushes the handle 20 upwardly and the jaw 26 downwardly such that the male ear tag member 30 is inserted through the piglet's ear into the female ear tag member 28. While the second operator is tagging the piglet, the first operator can load the male and female tag parts 28, 30 onto the second pliers 18. When the second person removes his/her foot from the depressed foot pedal 36, 38, the pedal automatically rises to a neutral position due to the weight of the arm assembly 42, which allows the arms 44, 46 to move downwardly and thereby open the jaws 24, 26 of the tool 18. The weight of the rod 46, which preferably is a solid steel bar, pivots the pedal back to a neutral position after each actuation or use. The first person can then reload a new male and female ear tag components on the first tool 18 while the second person uses the opposite foot pedal and tool to insert an ear tag into the ear of a second piglet.

The tool 18 has been modified to include a screw 52 which minimizes the pressure on the finger 32. This is advantageous since a piglet's ear is thin and risks being torn if a piglet is pulled away or moves prematurely while the tool is engaged or actuated. The reduced resistance on the finger 32 reduces ear tears. Since the lower jaw 24 remains stationary during the tagging procedure, the risk of tearing the piglet's ear is minimized.

An adjustment bolt 54 is provided on the side of the cart 12. The bolt 54 limits upward movement of the rod 46, to prevent damage to the pliers, such as an operator stepping down too hard on the foot pedal 36, 38.

Thus, the station 10 speeds up the ear-tagging process substantially compared to conventional ear-tagging methods. The station 10 also eliminates the back-straining bending over of the person holding the piglet. The foot actuated tool also eliminates the hand actuated tool, as in the prior art which required significant hand strength throughout the long process of tagging numerous piglets.

FIGS. 6-9 show an alternative embodiment of the ear tagging station, in accordance with the present invention. The station shown in FIGS. 6-9 functions the same as the station described for FIGS. 1-5. The alternative station 10A includes a cart or table 12A with wheels 13 which can be locked and unlocked for rolling the station. The station 10A includes a bin 14A mounted or held within the cart or table 12A. The bracket 16A is mounted to the cart or table 12A and supports the pliers 18A. The bracket 16A includes a lower leg 17 with an elongated slot (FIGS. 6 and 9) through which the arm 42 extends. The foot pedals 36A, 38A are pivotally mounted to the cart or table 12A via the axles 37A and include a roller 40A for engaging the lower arm 44A of the arm assembly 48A. A tray 56 may be provided on the cart 112 or 12A to hold the tag pieces 28,30 in the holes in the tray.

Figure 7:
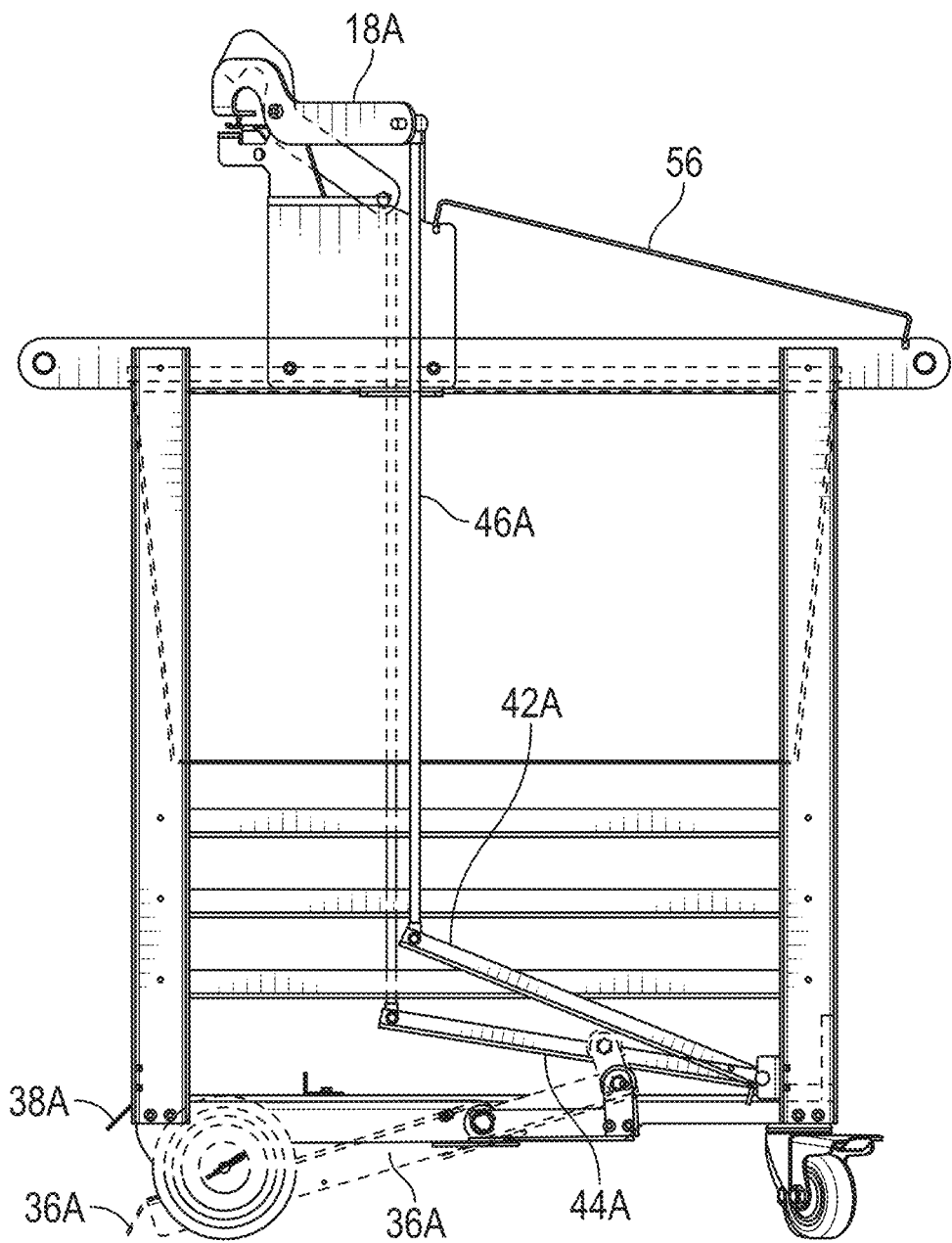
FIG. 7 is a side elevation view of the cart shown in FIG. 6, with the actuation position of the foot pedal, arm, and pliers shown in broken lines.
Figure 8:
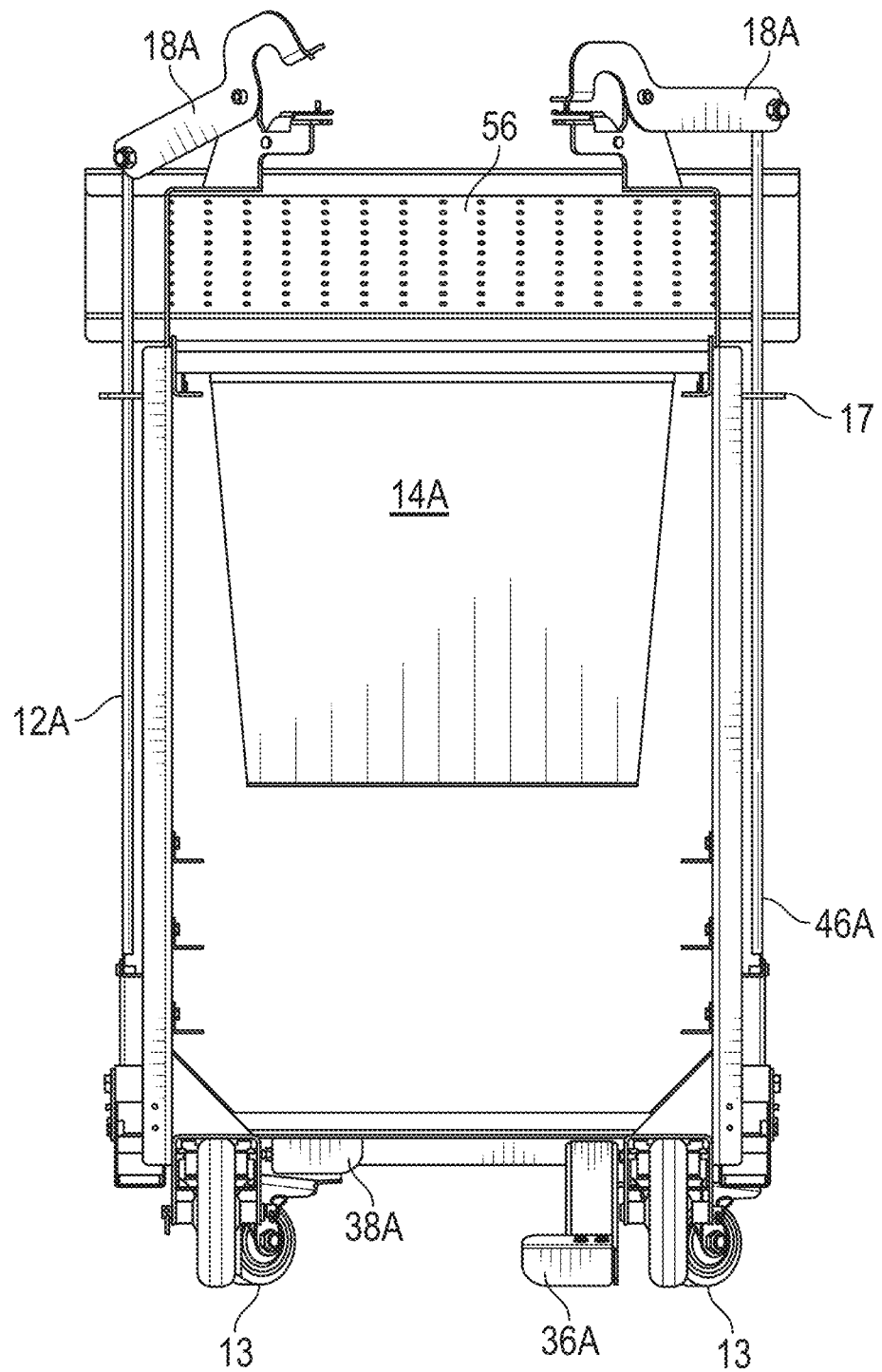
FIG. 8 is an end elevation view of the station shown in FIG. 6.
Figure 9:
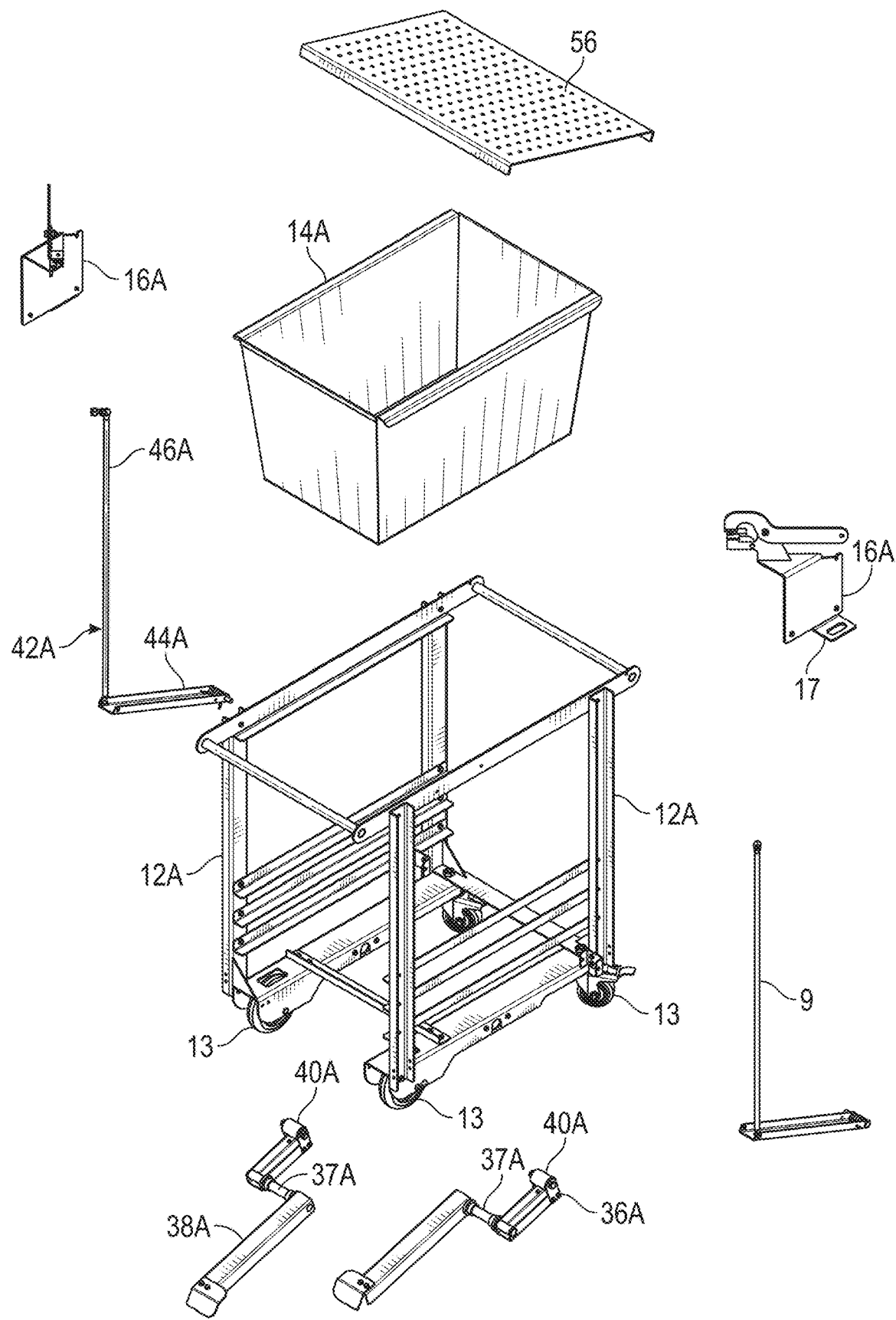
FIG. 9 is an excluded view of the station shown in FIG. 6.

As shown in FIG. 7, the foot pedals can be depressed by an operator's foot, which in turn lifts the lower arm 44A and vertical arm or rod 46A, which is slidable through the slot of the bracket leg 17, so as to actuate the pliers 18A. The broken line in FIG. 7 shows the foot pedal, arm assembly, and pliers in the neutral position, while the solid line show these components in the actuated position.

The invention has been shown and described above with the preferred embodiments, and it is understood that many modifications, substitutions, and additions may be made which are within the intended spirit and scope of the invention. From the foregoing, it can be seen that the present invention accomplishes at least all of its stated objectives.

What is claimed:

1. A piglet ear tagging station, comprising:
a cart;
left and right pliers on the cart adapted to hold male and female ear tag components;
left and right arms slidably mounted on the cart for vertical movement between a lowered position disengaged from the left and right pliers and a raised position engaging the left and right pliers, respectively;
left and right foot pedals pivotally mounted on the cart, and engaging the left and right arms, respectively, and being moveable between a neutral position which moves the arms to the lowered position and a depressed position which pushes the arms up to the raised position;
whereby depressing the left and right foot pedals actuates the left and right pliers, respectively, to install the male and female ear tag components on a piglet's ear.

2. The piglet ear tagging station of claim 1 wherein the left and right foot pedals are independently operable.

3. The piglet ear-tagging station of claim 1 further comprising a roller on top of each left and right arm to rollable engage the left and right pliers.

4. The piglet ear tagging station of claim 1 further comprising a tray to hold the ear tag components.

5. The piglet ear tagging station of claim 1 further comprising a roller on each of the foot pedals to engage the left and right arms.

6. The piglet ear tagging station of claim 1 wherein the arms have sufficient weight to move the pedals to the neutral position.

7. The piglet ear tagging station of claim 1 wherein the pliers include a screw to adjust pressure of the pliers.

8. The piglet ear tagging station of claim 1 further comprising bolts on the cart to adjust vertical movement of the arms.

9. The piglet ear tagging station of claim 1 wherein each plier has a handle adjacent an upper end of one of the arms.

* * * * *